United States Patent
Bohl

(10) Patent No.: US 11,419,651 B2
(45) Date of Patent: Aug. 23, 2022

(54) SYSTEMS AND METHODS FOR A PEDICLE SCREW ASSEMBLY WITH ANCHOR DEPLOYMENT

(71) Applicant: DIGNITY HEALTH, San Francisco, CA (US)

(72) Inventor: Michael A. Bohl, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 217 days.

(21) Appl. No.: 16/969,099

(22) PCT Filed: Feb. 14, 2019

(86) PCT No.: PCT/US2019/018070
§ 371 (c)(1),
(2) Date: Aug. 11, 2020

(87) PCT Pub. No.: WO2019/161100
PCT Pub. Date: Aug. 22, 2019

(65) Prior Publication Data
US 2021/0030453 A1    Feb. 4, 2021

Related U.S. Application Data

(60) Provisional application No. 62/630,300, filed on Feb. 14, 2018.

(51) Int. Cl.
*A61B 17/86* (2006.01)
*A61B 17/84* (2006.01)
*A61B 17/70* (2006.01)

(52) U.S. Cl.
CPC .......... *A61B 17/844* (2013.01); *A61B 17/864* (2013.01); *A61B 17/8625* (2013.01);
(Continued)

(58) Field of Classification Search
CPC . A61B 17/844; A61B 17/8625; A61B 17/864; A61B 17/8685; A61B 2017/8655
See application file for complete search history.

(56) References Cited

U.S. PATENT DOCUMENTS 5,976,139 A * 11/1999 Bramlet ............. A61B 17/8004
606/907
8,128,666 B2 * 3/2012 Falahee ............. A61B 17/7041
606/264

(Continued)

FOREIGN PATENT DOCUMENTS

WO     2017184892 A2    10/2017

OTHER PUBLICATIONS

International Search Report and Written Opinion issued in corresponding Application No. PCT/US2019/018070, dated May 9, 2019, 10 pages.

*Primary Examiner* — Kevin T Truong
*Assistant Examiner* — Tracy L Kamikawa
(74) *Attorney, Agent, or Firm* — Polsinelli PC

(57) ABSTRACT

Various embodiments of a pedicle screw assembly disclosed herein include a pedicle screw configured for engaging with bone tissue. The pedicle screw includes a body defining a plurality of channels through the body of the screw and in communication with a plurality of respective distal openings defined along the screw body. The pedicle screw assembly further includes an anchor defining a plurality of anchor members which are configured to be received at least partially through the plurality of channels and the plurality of respective distal openings to further engage the pedicle screw to the bone tissue.

7 Claims, 8 Drawing Sheets

(52) U.S. Cl.
CPC ...... *A61B 17/8685* (2013.01); *A61B 17/7035* (2013.01); *A61B 2017/8655* (2013.01)

(56) References Cited

U.S. PATENT DOCUMENTS

| | | | |
|---|---|---|---|
| 8,491,584 B1 * | 7/2013 | Fagan | A61B 17/7266 606/64 |
| 8,998,966 B2 * | 4/2015 | Yap | A61B 17/7064 606/305 |
| 2006/0241656 A1 | 10/2006 | Starksen et al. | |
| 2015/0051702 A1 | 2/2015 | Chatalgner et al. | |

* cited by examiner

SYSTEMS AND METHODS FOR A PEDICLE SCREW ASSEMBLY WITH ANCHOR DEPLOYMENT

CROSS REFERENCE TO RELATED APPLICATIONS

This is a PCT application that claims benefit to U.S. provisional application Ser. No. 62/630,300 filed on Feb. 14, 2018 which is incorporated by reference in its entirety.

FIELD

The present disclosure generally relates to surgical devices; and in particular, to systems and methods for pedicle screw assemblies.

BACKGROUND

Mechanical instability of the spine can result from many causes, including degenerative disease, trauma, infection, spinal deformity, or neoplastic processes. Left untreated, such spinal instability can result in pain, neurological compromise, and immobility. Spinal instability is treated surgically via fixation and fusion of the unstable spinal levels. Fixation of the spine is accomplished posteriorly through the insertion of screws through the vertebral pedicles, which are then segmentally connected by metal rods.

For patients undergoing spinal fixation and fusion surgery, pedicle screws are considered a standard of care. One of the most common complications associated with pedicle screw fixation, especially in long fixation constructs, is screw failure and pull-out with resultant pseudarthrosis or adjacent segment disease. Existing strategies for increasing the axial resistance required to pull out a pedicle screw include increased screw sizes, alternative core shapes, alternative thread shapes, and bone-cement augmentation. Each of these strategies comes with significant limitations, and none have proven to be a clinically reliable solution to the problem of pedicle screw failure.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Figure 1:
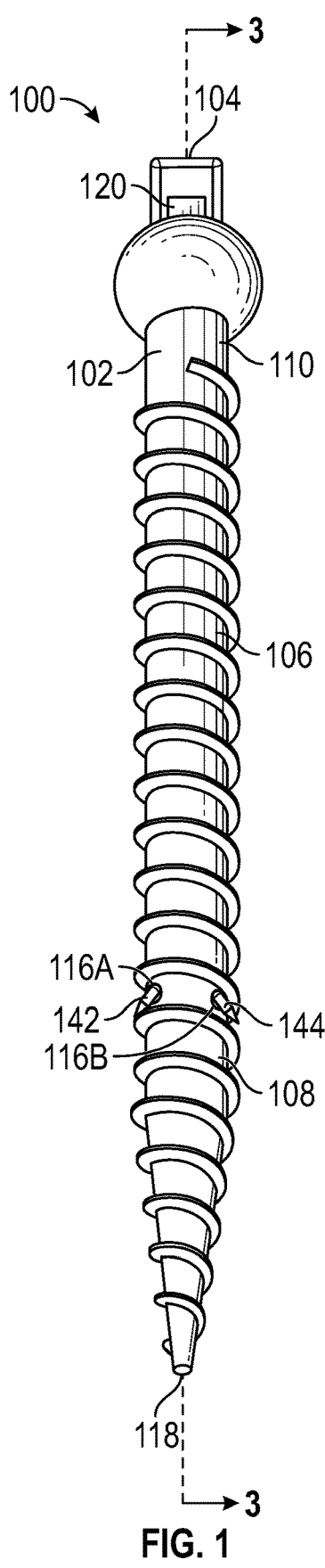
FIG. 1 is a perspective view of a first embodiment of a pedicle screw assembly having a pedicle screw and a bone anchor with integral anchor ends, according to one aspect of the present disclosure.

Various embodiments of a pedicle screw assembly having one or more bone anchors that are engaged along a pedicle screw for securing the pedicle screw within a pedicle of a vertebra are disclosed. In some embodiments, the pedicle screw assembly includes a pedicle screw having external threads configured to allow the pedicle screw to be partially engaged within a pedicle vertebra. In addition, various embodiments of the pedicle screw may include one or more channels in communication with respective distal openings configured to accommodate passage of bone anchor ends through the body of the pedicle screw as described herein. In some embodiments, the bone anchor ends may extrude outwardly from the pedicle screw when the bone anchor is in a post-deployment configuration, thereby driving the anchor ends within bone, which further engages the pedicle screw to the pedicle vertebra.

In some embodiments, the bone anchor generally includes an elongated anchor body defining a base and a pair of anchor members extending from the base, with at least a portion of the anchor body being bendable and/or flexible. The anchor members of the bone anchor are configured for insertion within the channels of the pedicle screw and further configured to drive the anchor ends into the bone tissue as described herein.

In one method of engaging a pedicle screw to bone or other target location, the pedicle screw is inserted into a pedicle of the vertebra and the bone anchor is inserted through the respective channels of the pedicle screw such that the anchor ends associated with the bone anchor extend outwardly from the pedicle screw in a post-deployment position and engage bone tissue, thereby further engaging the pedicle screw to the pedicle vertebra. Referring to the drawings, embodiments of a pedicle screw assembly are illustrated and generally indicated as 100 and 200 in FIGS. 1-14.

Figure 2:
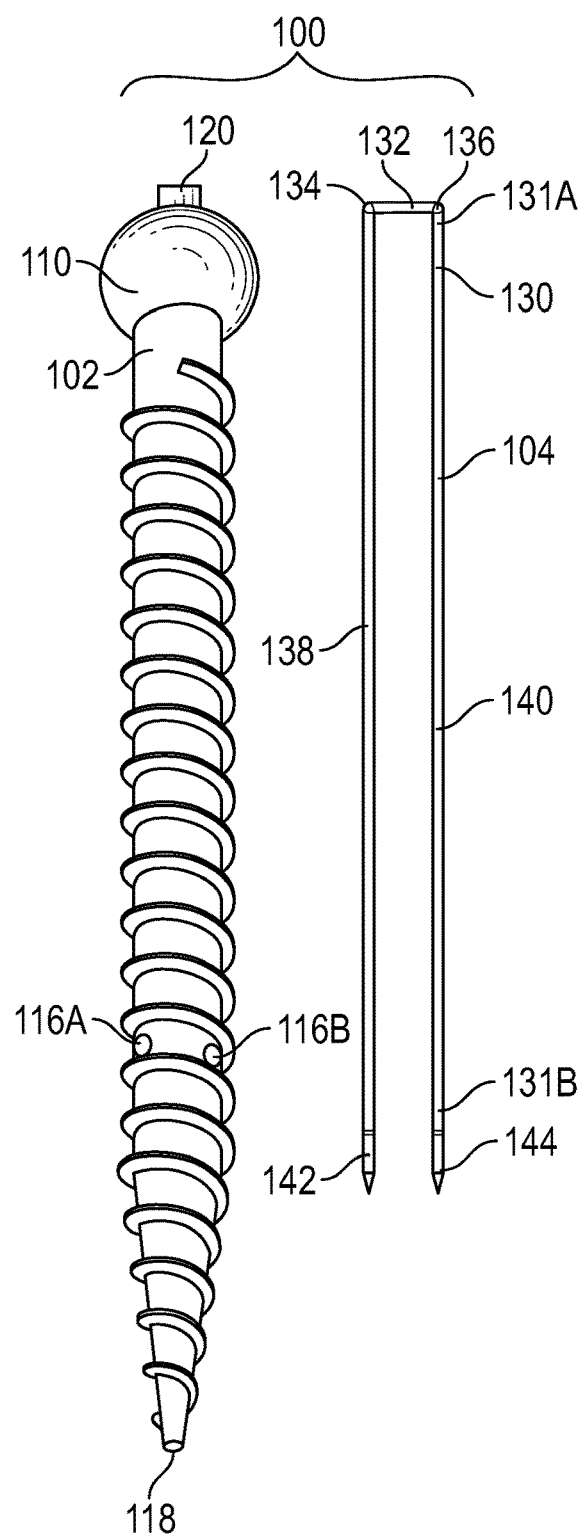
FIG. 2 is an exploded view of the pedicle screw assembly of FIG. 1 depicting the pedicle screw and the bone anchor, according to one aspect of the present disclosure.
Figure 3:
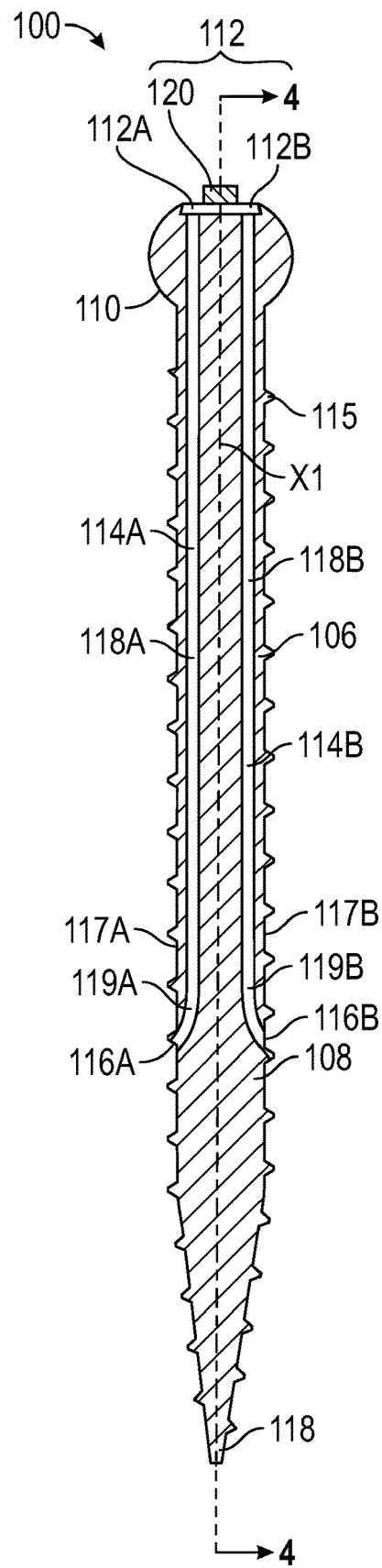
FIG. 3 is a cross-sectional view of the pedicle screw taken along line 3-3 of FIG. 1, according to one aspect of the present disclosure.

Referring to FIGS. 1-7, a first embodiment of a pedicle screw assembly, designated 100, is illustrated. As shown in FIGS. 1-3, the pedicle screw assembly 100 includes a pedicle screw 102 that is configured to be mechanically coupled to a bone anchor 104 in a manner that is suitable for anchoring the pedicle screw 102 to bodily tissue, such as the bone tissue of a vertebra. In some embodiments, the pedicle screw 102 general includes an elongated screw body 106 defining a distal portion 108 (including a conical tip 118 defined at the free end thereof) and a proximal portion 110 that defines a pair of proximal openings 112 (shown in FIG. 3); designated a first proximal opening 112A and second proximal opening 112B. As indicated in FIG. 3, the first proximal opening 112A is in communication with a first channel 114A formed at least partially along a longitudinal axis X1 of the pedicle screw 102, and the second proximal opening 112B is in communication with a second channel 114B formed at least partially along the longitudinal axis X1 of the pedicle screw 102. In some embodiments as shown, at least a portion of the first channel 114A is in parallel relation relative to the second channel 114B. Further, the screw body 106 may define a threaded portion 115 defining external threads that extends substantially along the length of the screw body 106 configured to accommodate the pedicle screw 102 to engage and be retained within bone tissue.

Referring to FIG. 3, along the distal portion 108 of the pedicle screw 102, the first channel 114A is in communication with a first distal opening 116A formed through a first lateral side 117A of the pedicle screw 102 along the distal portion 108 of the screw body 106, and the second channel 114B is in communication with a second distal opening 116B formed through a second lateral side 1178 of the pedicle screw 102 along the distal portion 108 of the screw body 106. In some embodiments, the first lateral side 117A of the pedicle screw 102 is generally defined opposite the second lateral side 117B of the pedicle screw 102 such that the first distal opening 116A is formed opposite the second distal opening 116B, but the present disclosure is not limited in this regard. In addition, as indicated, the first channel 114A may include a first portion 118A extending from the proximal portion 110 of the screw body 106, and a second portion 119A adjacent the first distal opening 116A. Similarly, the second channel 114B may include a first portion 118B extending from the proximal portion 110 of the screw body 106, and a second portion 119B adjacent the second distal opening 116B. Each of the second portion 119A and the second portion 119B may be configured to be at least partially non-linear, and may define a curve as shown or a bend away from the longitudinal axis X1 of the pedicle screw body 106. In this manner, the first channel 114A and the second channel 114B may define a general partial C-shape or arcuate shape configuration, a general partial Y-shape configuration (not shown), or T-shape configuration (not shown). It is contemplated that the first channel 114A and the second channel 114B may take on any form so long as the first channel 114A is in communication with the first distal opening 116A and the second channel 114B is in communication with the second distal opening 116B so that portions of the bone anchor 104 can traverse through the first channel 114A and extrude out the first distal opening 116A and portions of the bone anchor 104 can similarly traverse through the second channel 114B and extrude out the second distal opening 116B, as further described herein. In some embodiments, the first and second distal openings 116A and 116B may be defined, respectively, directly adjacent the first portion 118A and the first portion 118B (not shown), above the first portion 118A and the first portion 118B (not shown), below the first portion 118A and the first portion 118B as shown in FIG. 3, such that the first distal opening 116A the second distal opening 116B are oriented closer to the conical tip 118 of the pedicle screw 102 than the first portion 118A of the first channel 114A and the first portion 118B of the second channel 114B.

In addition, as shown in FIGS. 1-5, in some embodiments the pedicle screw 102 may include a stopper 120 for obstructing the movement of at least a portion of the bone anchor 104 relative to the screw body 106 in order to allow the bone anchor 104 to be removed from the screw body 106, as further described herein. The stopper 120 may generally define a block or ridge shaped-component formed along the proximal portion 110 of the screw body 106 between the first proximal opening 112A and the second proximal opening 112B as shown, and may comprise rubber, plastic, steel or any biocompatible material. In some embodiments, the stopper 120 may further be removable from the screw body 106 where, e.g., it is desired to permanently engage the bone anchor 104 to the screw body 106 and bone tissue.

Referring back to FIG. 2, in some embodiments the bone anchor 104 includes an anchor body 130, defining a proximal portion 131A and a distal portion 131B, with the anchor body 130 configured for at least partial insertion within the screw body 106 to engage the pedicle screw 102 to a pedicle or other target sites. In some embodiments, the anchor body 130 includes a base portion 132 along the proximal portion 131A of the anchor body 130, with the base portion 132 defining a first side 134 and a second side 136 opposite the first side 134, as indicated. The base portion 132 may generally define a cuboidal or cylindrically shaped configuration and may be manufactured in any number of ways sufficient to receive a force (F in FIG. 4) for driving the bone anchor 104 partially through the screw body 106, as further described herein. For example, the base portion 132 may include a handle or thumb print to receive a force applied by a human hand, or may define a rigid surface for receiving a force applied by a blunt instrument such as a hammer.

As shown, the anchor body 130 may further include a first anchor member 138 extending orthogonally from the first side 134 of the base portion 132 and configured for insertion within the first channel 114A of the screw body 106. Similarly, the anchor body 130 may include a second anchor member 140 extending orthogonally from the second side 136 of the base portion 132 and configured for insertion within the second channel 114B. In some embodiments, the first anchor member 138 is in substantially parallel relation relative to the second anchor member 140, as in the case where at least a portion of the first channel 114A and the second channel 114B define a similar parallel configuration, but the present disclosure is not limited in this regard. In general, the first anchor member 138 and the second anchor member 140 may define any shape suitable for insertion within the first channel 114A and the second channel 114B of the screw body 106, respectively. For example, the first anchor member 138 and the second anchor member 140 may be generally cylindrical in shape, may define planar plates or tabs, may define spikes, etc., and may be formed with any biocompatible material, one or more metals, plastics, or combinations thereof. In addition, while two anchor members (the first anchor member 138 and the second anchor member 140) are shown, the anchor body 130 may define a sole anchor member (not shown) or any number of anchor members as desired (not shown). At least a portion of the anchor body 130, including e.g., the first anchor member 138 and the second anchor member 140 may be at least partially bendable, biasable, and/or flexible to accommodate passage of the first anchor member 138 and the second anchor member 140 through the first channel 114A and the second channel 114B, respectively.

In addition, the first anchor member 138 may define an anchor end 142, and the second anchor member 140 may define an anchor end 144 along the distal portion 131B of the anchor body 130. The anchor end 142 and the anchor end 144 may define any number of shapes or configurations, may be cylindrical in shape, may define planar plates or tabs, and/or may define spikes or blades, etc., such that the anchor end 142 and the anchor end 144 can penetrate bone tissue. In some embodiments, the anchor end 142 and the anchor end 144 are integral with the first anchor member 138 and the second anchor member 140, respectively. In some embodiments, the anchor end 142 and the anchor end 144 define a general tapered shape configuration.

Figure 4:
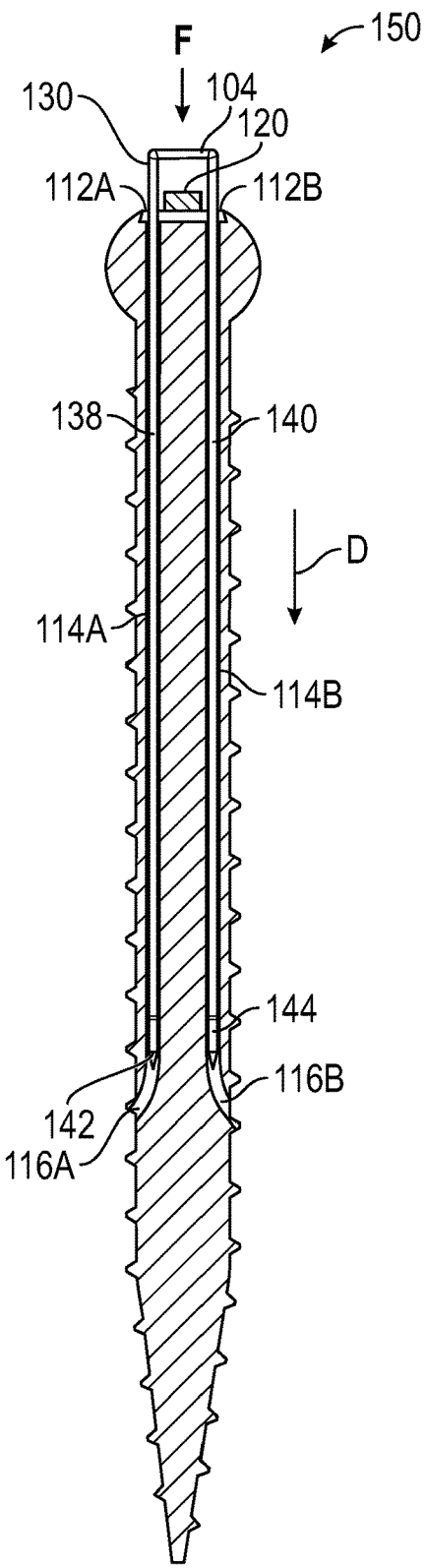
FIG. 4 is a cross-sectional view of the pedicle screw of FIG. 3 taken along line 4-4 showing the bone anchor disposed partially within a channel of the pedicle screw, according to one aspect of the present disclosure.
Figure 5:
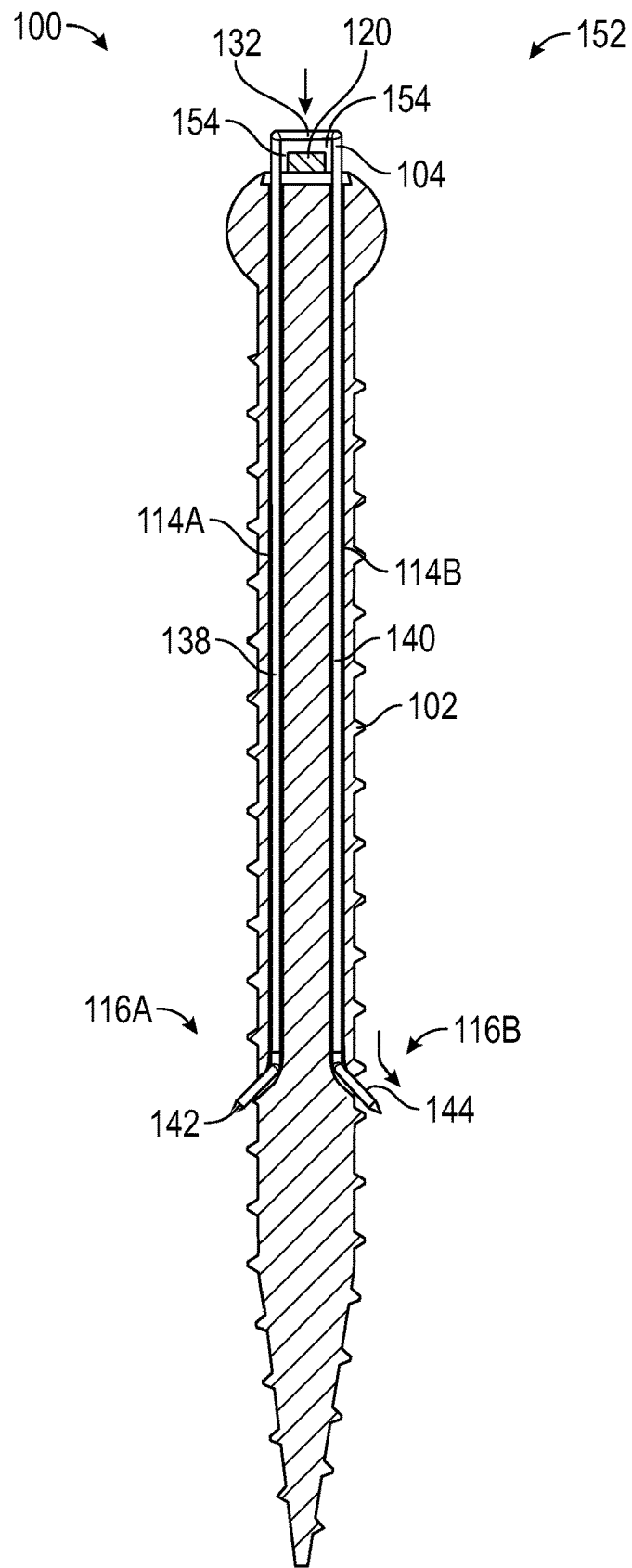
FIG. 5 is a cross-sectional view of the pedicle screw of FIG. 3 showing the bone anchor disposed fully within the channel of the pedicle screw and deployed through an opening formed at the distal end of the pedicle screw, according to one aspect of the present disclosure.
Figure 6:
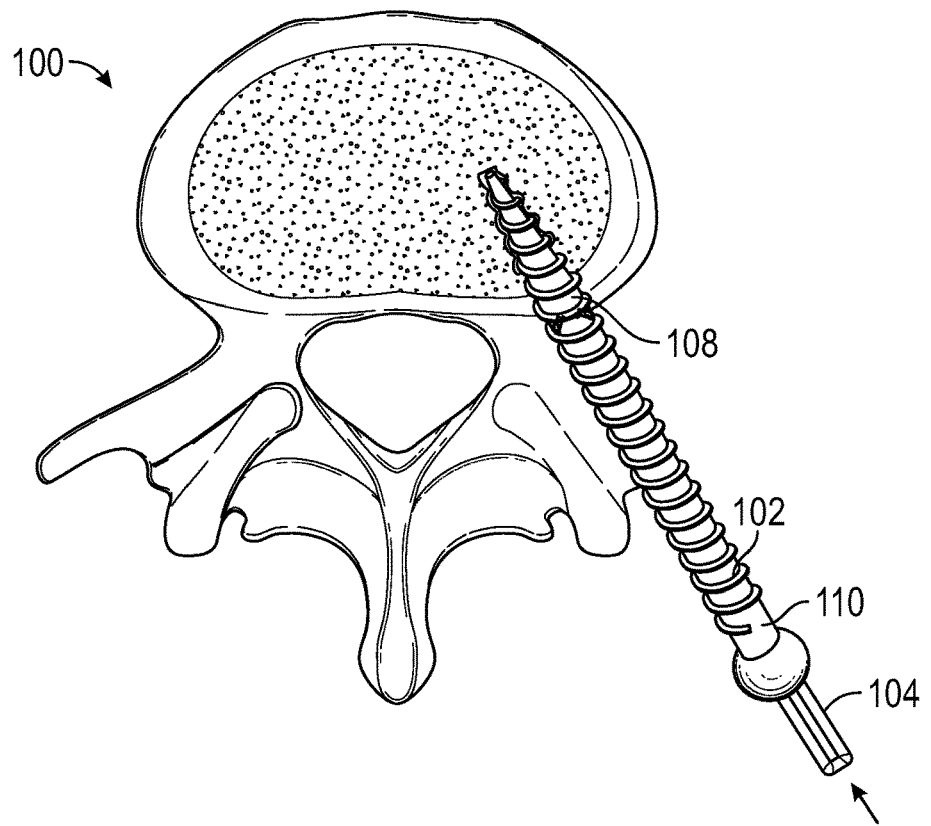
FIG. 6 is an anatomical perspective view of the pedicle screw partially engaged inside a pedicle of a vertebra with the bone anchor in a pre-deployment position, according to one aspect of the present disclosure.

Referring to FIGS. 4-7, one method of implanting the pedicle screw assembly 100 is illustrated. As shown in FIG. 6, the pedicle screw 102 is first engaged into bone tissue, such as a pedicle of the vertebra, so that the proximal portion 110 of the pedicle screw 102 extends from the bone tissue. Once the pedicle screw 102 is implanted into the bone tissue, the first anchor member 138 and the second anchor member 140 of the bone anchor 104 are inserted into the first proximal opening 112A and the second proximal opening 112B, respectively, of the pedicle screw 102, in the manner indicated in FIG. 4 to form a pre-deployment configuration 150 of the pedicle screw assembly 100.

Once the pre-deployment configuration 150 is formed, the first anchor member 138 is at least partially disposed within the first channel 114A, and the second anchor member 140 is at least partially disposed within the second channel 114B as shown in FIG. 4. Thereafter, in some embodiments, a force F may be applied as shown to drive the first anchor member 138 further through the first channel 114A and simultaneously drive the second anchor member 140 further through the second channel 114B in the direction D1. In some embodiments, the force F may be applied to the base portion 132 of the anchor body 130 by a hammer or other blunt instrument (not shown).

Figure 7:
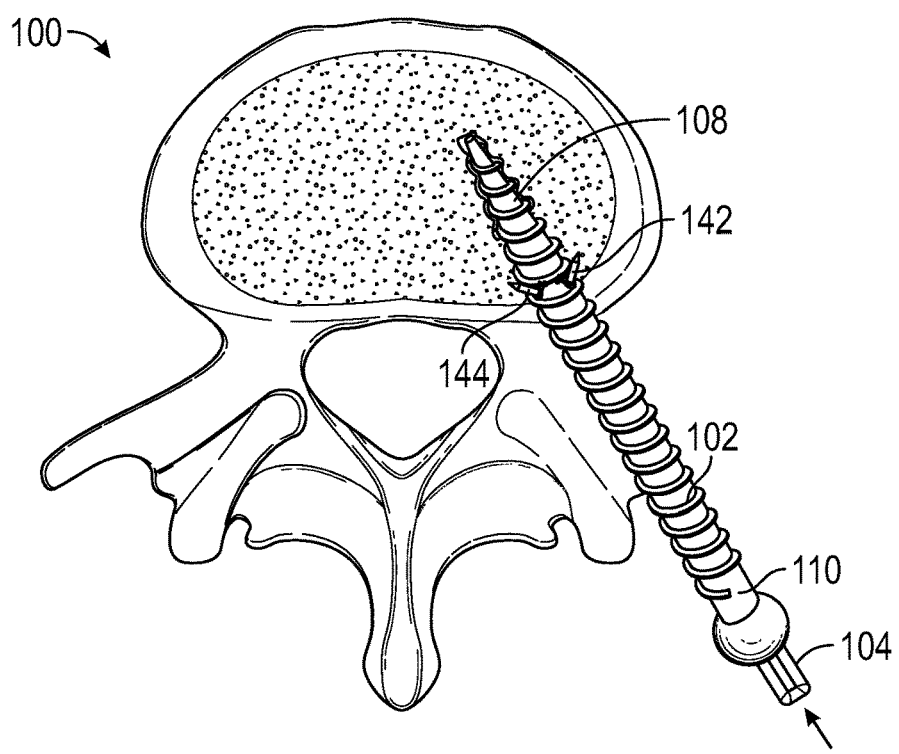
FIG. 7 is an anatomical perspective view of the pedicle screw partially engaged inside a pedicle vertebra with the anchor in a post-deployment position, according to one aspect of the present disclosure.
Figure 8:
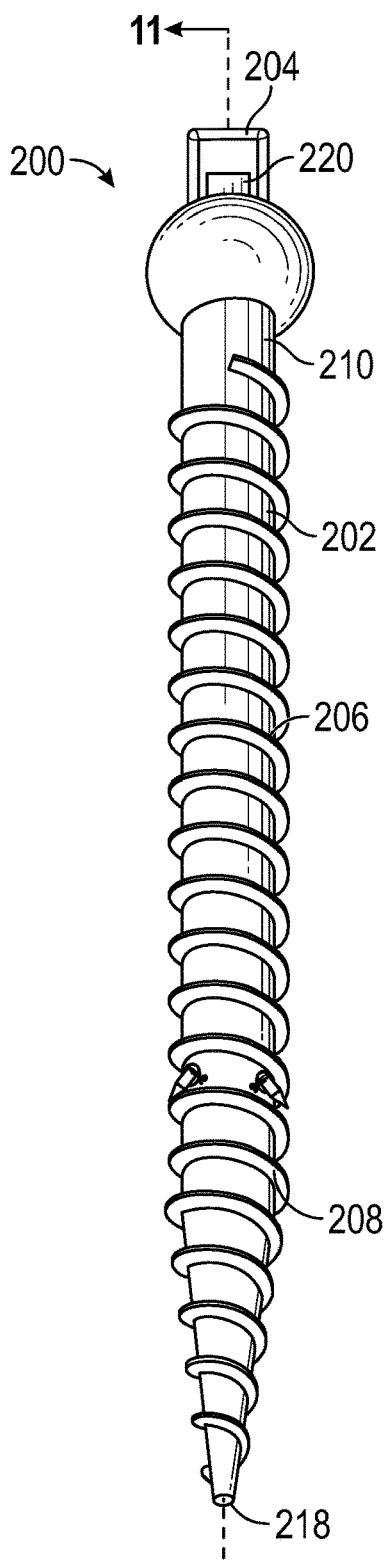
FIG. 8 is a perspective view of a second embodiment of a pedicle screw assembly having a pedicle screw, a bone anchor, and anchor ends, according to one aspect of the present disclosure.
Figure 9:
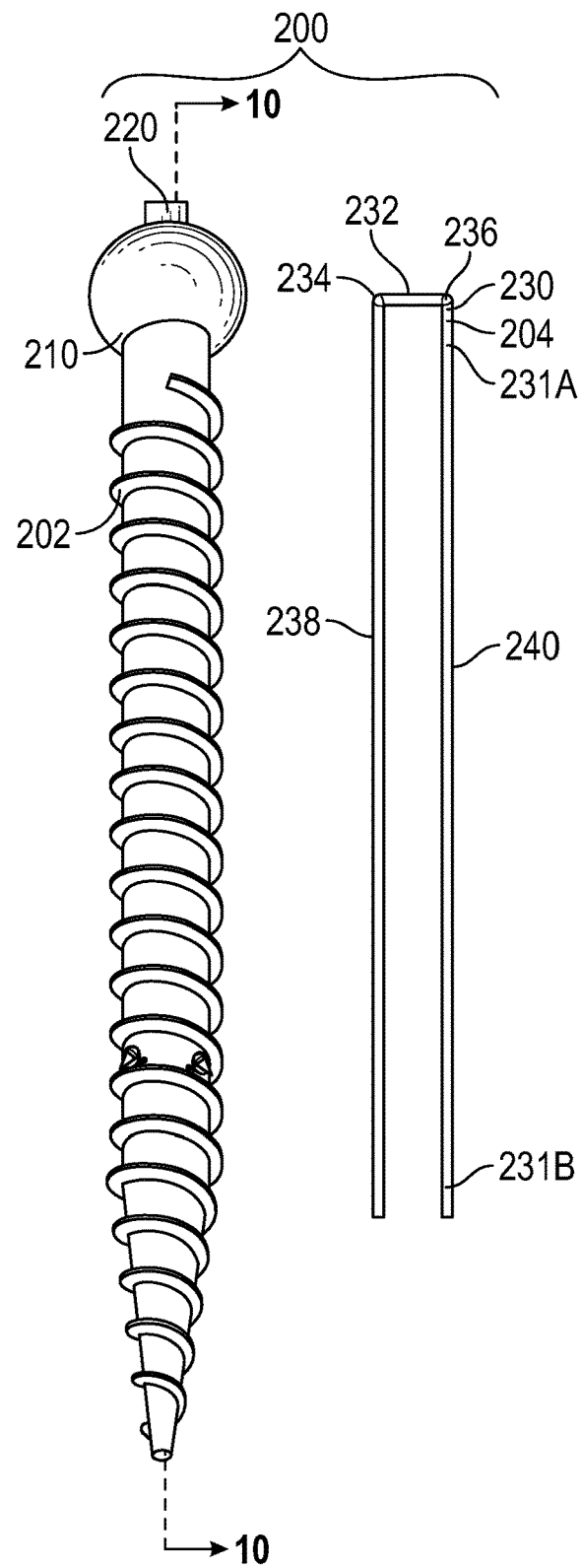
FIG. 9 is an exploded view of the pedicle screw assembly of FIG. 8 depicting the pedicle screw and the bone anchor, according to one aspect of the present disclosure.

Referring to FIG. 5 and FIG. 7, the application of the force F shifts the pedicle screw assembly 100 from the pre-deployment configuration 150 to a post-deployment configuration 152. In this post-deployment configuration 152, the anchor end 142 of the first anchor member 138 is extruded from the first distal opening 116A, and the anchor end 144 is extruded from the second distal opening 116B as shown in FIG. 5, which drives the anchor end 142 and the anchor end 144 into bone tissue as shown in FIG. 7. In some embodiments, when the pedicle screw 102 includes the stopper 120, the base portion 132 may contact the stopper 120 and limit the depth to which the first anchor member 138 and the second anchor member 140 can be passed within the first channel 114A and the second channel 114B respectively in the direction D1. In addition, in some embodiments, an axial gap 154 may be formed around the stopper 120. In this manner, a pair of plyers, hook, hammer, or other such instrument (not shown) may be engaged to the base portion 132 by maneuvering around the axial gap 154 when the pedicle screw assembly 100 is in the post-deployment configuration 152, and the bone anchor 104 may be pulled away from the pedicle screw 102 in a direction opposite D1 (not shown), thereby removing the first anchor member 138 from within the first channel 114A and removing the second anchor member 140 from within the second channel 114B. Disengagement of the bone anchor 104 from the pedicle screw 102 in this manner may be advantageous where implementation of the pedicle screw assembly 100 is no longer desired or needs to be removed from the bone tissue for whatever reason.

Referring to FIGS. 8-14, a second embodiment of the pedicle screw assembly, designated 200, is illustrated. As shown in FIGS. 8-11, the pedicle screw assembly 200 includes a pedicle screw 202 that is configured to be mechanically coupled to a bone anchor 204 in a manner that is suitable for anchoring the pedicle screw 202 to bodily tissue, such as the bone tissue of a vertebra. In some embodiments, the pedicle screw 202 generally includes an elongated screw body 206 defining a distal portion 208 (including a conical tip 218 at the free end thereof) and a proximal portion 210 that defines a pair of proximal openings 212; including a first proximal opening 212A and second proximal opening 212B. As indicated, the first proximal opening 212A is in communication with a first channel 214A formed at least partially along a longitudinal axis X2 of the pedicle screw 202, and the second proximal opening 212B is in communication with a second channel 214B formed at least partially along the longitudinal axis X2 of the pedicle screw 202. In some embodiments as shown, at least a portion of the first channel 214A is in parallel relation relative to the second channel 214B. Further, the screw body 206 may define a threaded portion 215 that extends substantially along the length of the screw body 206 configured to accommodate the pedicle screw 202 to engage and be retained within bone tissue.

Figure 10:
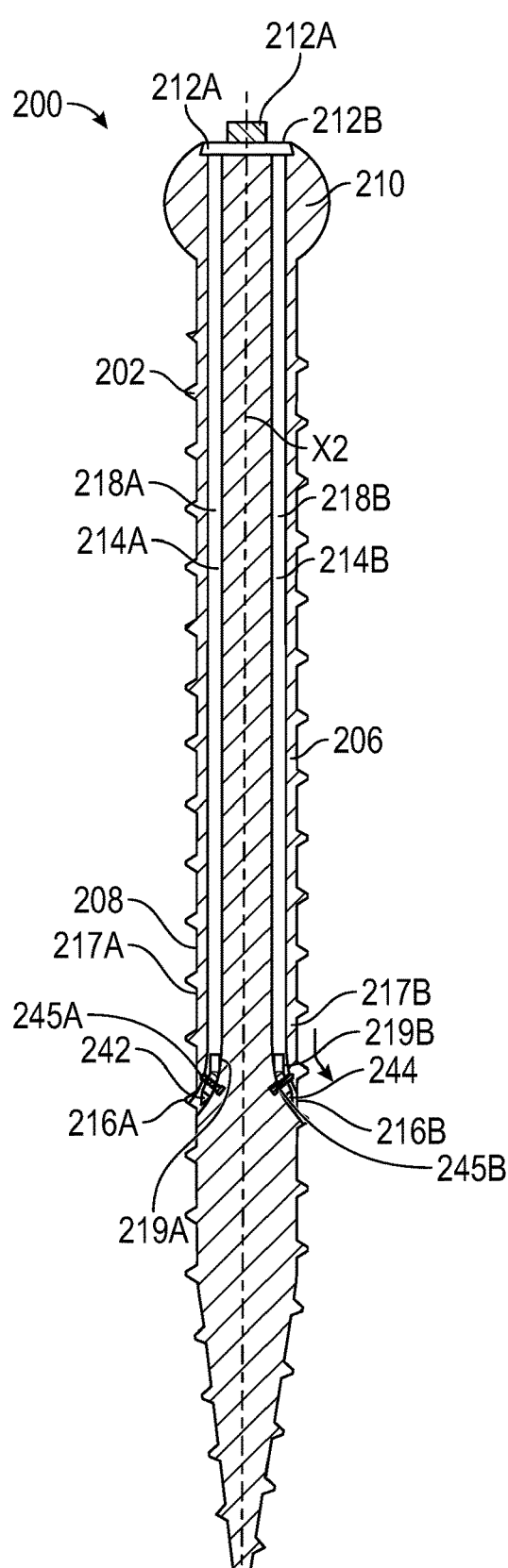
FIG. 10 is a cross-sectional view of the pedicle screw of FIG. 9 taken along line 10-10, according to one aspect of the present disclosure.
Figure 11:
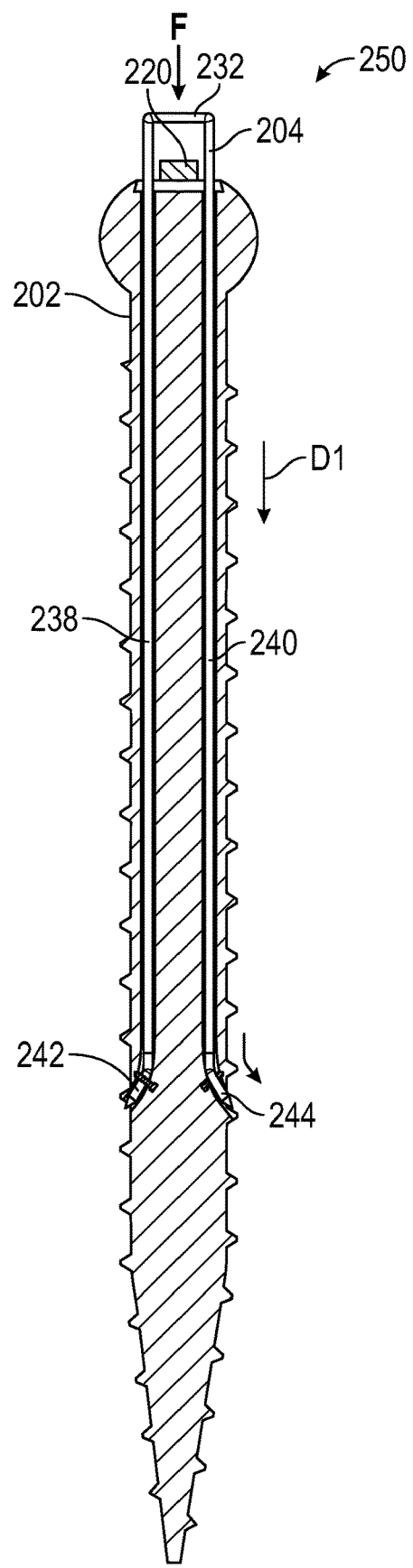
FIG. 11 is a cross-sectional view of the pedicle screw of FIG. 8 taken along line 11-11 showing the bone anchor disposed partially within a channel of the pedicle screw, according to one aspect of the present disclosure.

Referring to FIG. 10, along the distal portion 208 of the pedicle screw 202, the first channel 214A is in communication with a first distal opening 216A formed through a first lateral side 217A of the pedicle screw 202 along the distal portion 208 of the screw body 206, and the second channel 214B is in communication with a second distal opening 216B formed through a second lateral side 217B of the pedicle screw 202 along the distal portion 208 of the screw body 206. In some embodiments, the first lateral side 217A of the pedicle screw 202 is generally defined opposite the second lateral side 217B of the pedicle screw 202 such that the first distal opening 216A is formed opposite the second distal opening 216B, but the present disclosure is not limited in this regard. In addition, as indicated, the first channel 214A may include a first portion 218A extending from the proximal portion 210 of the screw body 206, and a second portion 219A adjacent the first distal opening 216A. Similarly, the second channel 114B may include a first portion 218B extending from the proximal portion 210 of the screw body 206, and a second portion 219B adjacent the second distal opening 216B. Each of the second portion 219A and the second portion 219B may be at least partially non-linear, and may define a curve as shown or a bend away from the longitudinal axis X2 of the pedicle screw body 206. In this manner, the first channel 214A and the second channel 214B may define a general partial C-shape or arcuate shape configuration, a general partial Y-shape configuration (not shown), or T-shape configuration (not shown). It is contemplated that the first channel 214A and the second channel 214B may take on any form so long as the first channel 214A is in communication with the first distal opening 216A and the second channel 214B is in communication with the second distal opening 216B so that portions of the bone anchor 204 can traverse through the first channel 214A and portions of the bone anchor 204 can traverse through the second channel 214B, as further described herein. In some embodiments, the first distal opening 216A the second distal opening 216B may be defined, respectively, directly adjacent the first portion 218A and the first portion 218B (not shown), may be defined above the first portion 218A and the first portion 218B (not shown), or may be defined below the first portion 218A and the first portion 218B as shown in FIG. 10, such that the first distal opening 216A the second distal opening 216B are oriented closer to the conical tip 218 of the pedicle screw 202 than the first portion 218A of the first channel 214A and the first portion 218B of the second channel 214B.

In addition, the pedicle screw 202 may include a stopper 220 for obstructing the movement of at least a portion of the bone anchor 204 relative to the screw body 206 in order to allow the bone anchor 204 to be removed from the screw body 206, as further described herein. The stopper 220 may generally define a block or ridge shaped-component formed along the proximal portion 210 of the screw body 206 between the first proximal opening 212A and the second proximal opening 212B as shown, and may be formed from rubber, plastic, steel or any biocompatible material. In some embodiments, the stopper 220 may further be removable from the screw body 206 where, e.g., it is desired to permanently engage the bone anchor 204 to the screw body 206 and bone tissue.

Referring back to FIG. 9, in some embodiments the bone anchor 204 includes an anchor body 230, defining a proximal portion 231A and a distal portion 231B, with the anchor body 230 configured for at least partial insertion within the screw body 206 to engage the pedicle screw 202 to a pedicle or other target site. In some embodiments, the anchor body 230 includes a base portion 232 along the proximal portion 231A of the anchor body 230, with the base portion 232 defining a first side 234 and a second side 236 opposite the first side 234 as indicated. The base portion 232 may generally define a cuboidal or cylindrically shaped configuration and may be manufactured in any number of ways sufficient to receive a force (F in FIG. 11) for driving the bone anchor 204 partially through the screw body 206, as further described herein. For example, the base portion 232 may include a handle or thumb print to receive a force applied by a human hand, or may define a rigid surface for receiving a force applied by a blunt instrument such as a hammer.

As shown, the anchor body 230 may further include a first anchor member 238 extending orthogonally from the first side 234 of the base portion 232 and configured for insertion within the first channel 214A. Similarly, the anchor body 230 includes a second anchor member 240 extending orthogonally from the second side 236 of the base portion 232 and configured for insertion within the second channel 214B. In some embodiments, the first anchor member 238 is in parallel relation relative to the second anchor member 240, as in the case where at least a portion of the first channel 214A and the second channel 214B define a similar parallel configuration, but the present disclosure is not limited in this regard. In general, the first anchor member 238 and the second anchor member 240 define any shape suitable for insertion within the first channel 214A and the second channel 214B of the screw body 206, respectively. For example, the first anchor member 238 and the second anchor member 240 may be generally cylindrical in shape, may define planar plates or tabs, may define spikes, etc., and may be formed with any biocompatible material, one or more metals, plastics, or combinations thereof. In addition, while two anchor members (the first anchor member 238 and the second anchor member 240) are shown, the anchor body 230 may define a sole anchor member (not shown) for engaging a sole channel of the screw body 206 (not shown) or any number of anchor members as desired (not shown). At least a portion of the anchor body 230, including e.g., the first anchor member 238 and the second anchor member 240 may be at least partially bendable or flexible to accommodate passage of the first anchor member 238 and the second anchor member 240 at least partially through the first channel 214A and the second channel 214B, respectively.

Referring to FIGS. 8-12 and FIG. 14, the pedicle screw assembly 200 may further include an anchor end 242 staged within the second portion 219A of the first channel 214A, and a second anchor end 244 staged within the second portion 219B of the second channel 214B. In this embodiment of the pedicle screw assembly 200, the anchor end 242 and the anchor end 244 are not formed integrally with the anchor body 130, but are instead disposed within the first and second channels 214A and 214B of the screw body 206 as indicated. The anchor end 242 may be staged just inside the screw body 206 within the second portion 219A directly adjacent to the distal opening 216A, and the anchor end 244 may be staged just inside the screw body 206 within the second portion 219B directly adjacent to the distal opening 216B as shown in FIG. 10. As further described herein, when the anchor 204 is engaged to the pedicle screw body 206 (i.e., the first anchor member 238 is driven through the first channel 214A and the second anchor member 240 is concurrently driven through the second channel 214B), the first anchor member 238 drives the anchor end 242 at least partially through the first distal opening 216A, and concurrently the second anchor member 240 drives the anchor end 244 at least partially through the second distal opening 216B. The anchor end 242 and the anchor end 244 may define any number of shapes or configurations, may be cylindrical in shape, may define planar plates or tabs, and/or may define spikes or blades, etc., such that the anchor end 242 and the anchor end 244 can penetrate bone tissue. In some embodiments, the anchor end 242 and the anchor end 244 define a general tapered shape configuration.

As further indicated in FIG. 10, the pedicle screw assembly 200 may include a first tether member 245A and a second tether member 245B. The first tether member 245A may be engaged to the anchor end 242 and the screw body 206 within the channel 214A, and the second tether member 245B may be engaged to the anchor end 244 and the screw body 206 within the channel 214B. The first tether member 245A and the second tether member 245B may comprise a rubber member or other such flexible component. In use, the first tether member 245A restricts a predetermined degree of movement of the anchor end 242 relative to the screw body 206 so that the anchor end 242 does not merely fall outside the distal opening 216A and the first channel 214A, and the second tether member 245B restricts a predetermined degree of movement of the anchor end 244 relative to the screw body 206 so that the anchor end 244 does not merely fall outside the distal opening 216B and the second channel 214B.

Figure 12:
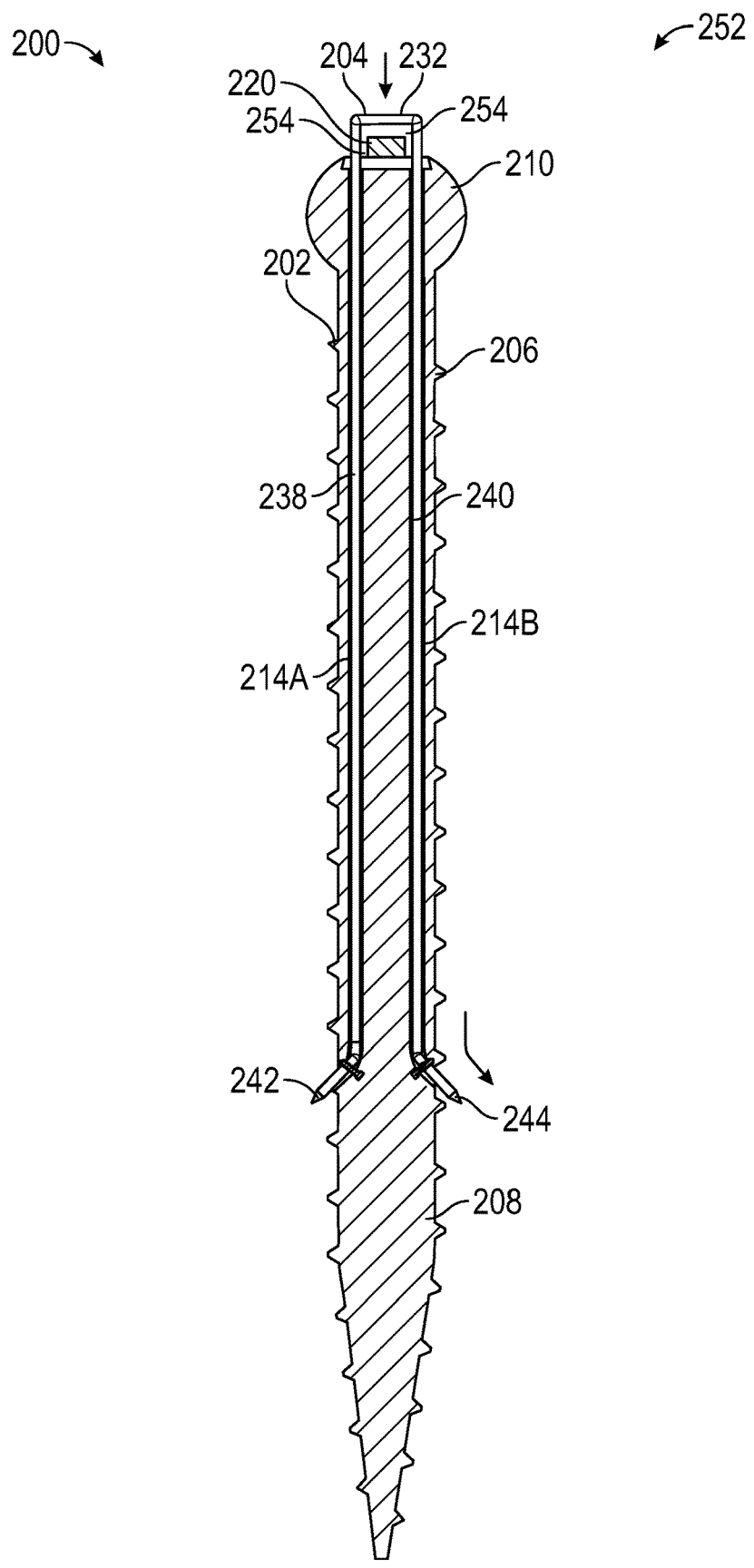
FIG. 12 is a cross-sectional view of the pedicle screw of FIG. 8 showing the bone anchor disposed fully within the channel of the pedicle screw and deployed through an opening formed at the distal end of the pedicle screw, according to one aspect of the present disclosure.
Figure 13:
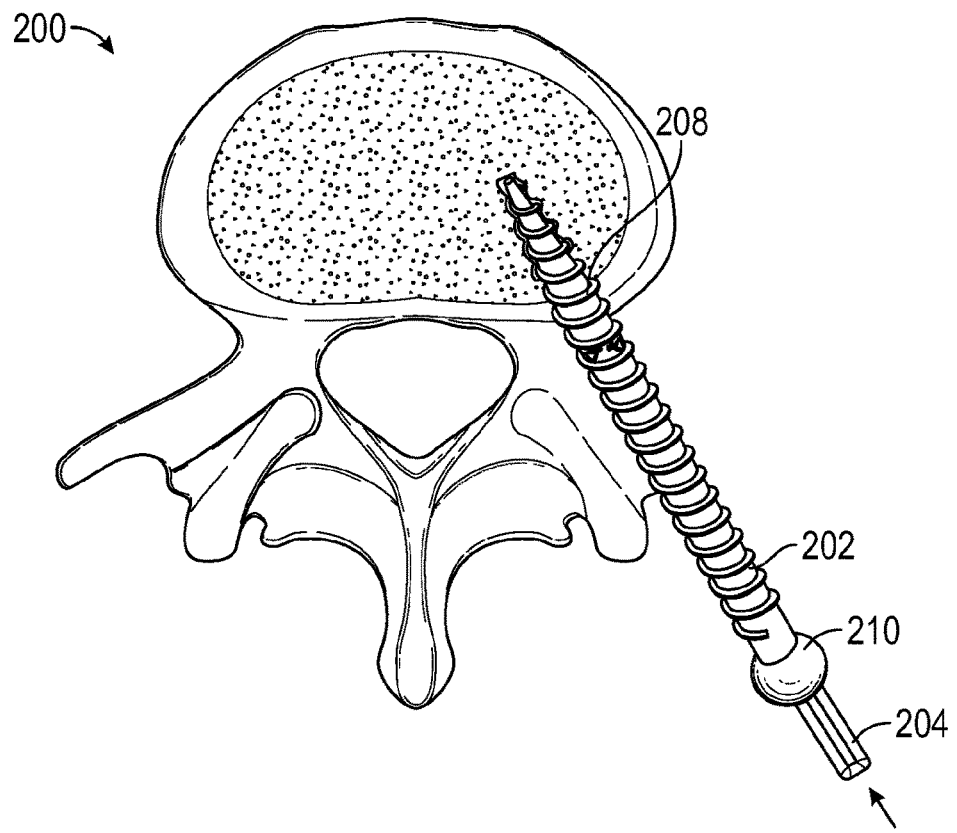
FIG. 13 is an anatomical perspective view of the pedicle screw partially engaged inside a pedicle vertebra with the bone anchor in a pre-deployment position, according to one aspect of the present disclosure.

Referring to FIGS. 11-14, one method of implanting the pedicle screw assembly 200 is illustrated. As shown in FIG. 13, the pedicle screw 202 is first engaged into bone tissue, such as a pedicle of the vertebra, such that the proximal portion 210 of the pedicle screw 202 extends from the bone tissue. Once the pedicle screw 202 is implanted into the bone tissue, the first anchor member 238 and the second anchor member 240 of the bone anchor 204 are inserted into the first proximal opening 212A and the second proximal opening 212B, respectively, of the pedicle screw 202, in the manner indicated in FIG. 11 to form a pre-deployment configuration 250 of the pedicle screw assembly 200. In this manner, the terminal ends of the first anchor member 238 and the second anchor member 240 contact the anchor end 242 and the anchor end 244, respectively, as shown.

Once the pre-deployment configuration 250 is formed, and the first anchor member 238 is at least partially received within the first channel 214A as indicated, and the second anchor member 240 is at least partially received within the second channel 214B, a force F may be applied as shown to drive the first anchor member 238 against the first anchor end 242 and concurrently drive the second anchor member 240 against the second anchor end 244 in the direction D1, thereby causing the anchor end 242 and the anchor end 244 to at least partially extrude through the distal opening 216A and the distal opening 216B, respectively. The force F may be applied to the base portion 232 of the anchor body 230 by a hammer or other blunt instrument (not shown).

Figure 14:
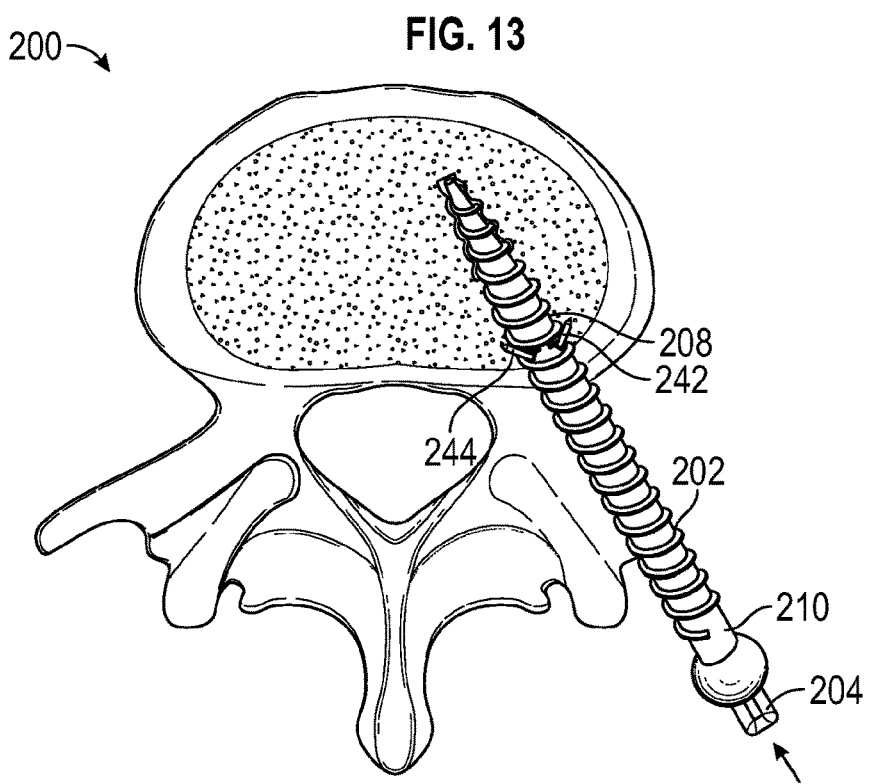
FIG. 14 is an anatomical perspective view of the pedicle screw partially engaged inside a pedicle vertebra with the anchor in a post-deployment position, according to one aspect of the present disclosure.

Referring to FIG. 12 and FIG. 14, the application of the force F shifts the pedicle screw assembly 200 from the pre-deployment configuration 250 to a post-deployment configuration 252. In this post-deployment configuration 252, at least a portion of the anchor end 242 is extruded outside the first distal opening 216A, and at least a portion of the anchor end 244 is extruded outside the second distal opening 216B as shown in FIG. 12, which drives the anchor end 242 and the anchor end 244 into bone tissue as shown in FIG. 14. In some embodiments, when the pedicle screw 202 includes the stopper 220, the base portion 232 may contact the stopper 220 and limit the depth to which the first anchor member 238 and the second anchor member 240 can traverse the first channel 214A and the second channel 214B respectively in the direction D1. In addition, in some embodiments, an axial gap 254 may be formed around the stopper 220. In this manner, a pair of plyers, hook, hammer, or other such instrument (not shown) may be engaged to the base portion 232 by maneuvering around the axial gap 254 when the pedicle screw assembly 200 is in the post-deployment configuration 252, and the bone anchor 204 may be pulled away from the pedicle screw 202 in a direction opposite D1 (not shown), thereby removing the first anchor member 238 from within the first channel 214A and removing the second anchor member 240 from within the second channel 214B. Disengagement of the bone anchor 204 from the pedicle screw 202 in this manner may be advantageous where, e.g., it is desired to re-use the anchor 204 for other similar applications.

In some embodiments, the pedicle screw assemblies 100 and 200 are configured to be affixed to the larger vertebrae of the lumbar spine, or the smaller vertebrae of the thoracic or cervical spine.

In some embodiments, the pedicle screw assemblies 100 and 200 may be made from a metal, such as titanium, or a metal-based alloy, such as titanium-based alloy. Alternatively, the pedicle screw assemblies 100 and 200 may comprise a reinforced polymer material. In some embodiments, the material used to manufacture the pedicle screw assemblies 100 and 200 can have a high bioactivity and high flexibility, and a result, can improve ingrowth and mechanical fixation.

In some embodiments, the pedicle screws 102 and 202 may be engaged to a tulip structure (not shown) which is configured to interface with a longitudinal bar or a plate. In some embodiments, the tulip structure can be flexibly coupled to the pedicle screws 102 and 202 by way of a ball-joint or other type of flexible joint such that the pedicle screw assemblies 100 and 200 can account for any bending of the individual's spine while still exerting an axial force on the longitudinal bar, thereby stabilizing the spine of the individual.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A pedicle screw assembly, comprising:
    a pedicle screw, comprising
        a screw body defining a proximal portion and a distal portion,
        a first channel and a second channel defined within the screw body, each of the first and second channels including a first portion extending parallel to a longitudinal axis of the screw body and a second portion that is curved away from the respective first portion and the longitudinal axis of the screw body, the first and second channels not in communication with each other,
        a first opening defined along a first lateral side of the screw body and in communication with the first channel,
        a second opening defined along a second lateral side of the screw body and in communication with the second channel; and
    an anchor defining an anchor body configured for being partially disposed within the screw body to engage the pedicle screw to a surgical site, the anchor body comprising:
        a base portion defining a first side and a second side opposite the first side,
        a first anchor member integral with and extending orthogonally from the first side of the base portion and configured for insertion within the first channel of the pedicle screw, and
        a second anchor member integral with and extending orthogonally from the second side of the base portion and configured for insertion within the second channel of the pedicle screw.

2. The pedicle screw assembly of claim 1, further comprising:
    a first anchor end oriented along the first anchor member, and
    a second anchor end oriented along the second anchor member, the first anchor end and the second anchor end being configured for penetrating bone tissue.

3. The pedicle screw assembly of claim 2, wherein the first anchor end and the second anchor end are integral with the anchor body.

4. The pedicle screw assembly of claim 2, wherein the first anchor end and the second anchor end are separate from the anchor body, and engage the first anchor member and the second anchor member respectively as the first anchor member and the second anchor member are inserted within the first channel and the second channel respectively.

5. The pedicle screw assembly of claim 1, wherein at least a portion of the first anchor member and at least a portion of the second anchor member is flexible such that the first anchor member and the second anchor member are flexible relative to the base portion to accommodate passage of the first anchor member and the second anchor member through the first channel and the second channel, respectively.

6. The pedicle screw assembly of claim 1, further comprising:
   a first anchor end staged within the first channel; and
   a second anchor end staged within the second channel,
   wherein the anchor is configured to drive the first anchor end partially through the first opening and further configured to drive the second anchor end partially through the second opening.

7. The pedicle screw assembly of claim 6, further comprising:
   a tether member coupling the first anchor end to the screw body that limits movement of the first anchor end relative to the screw body.

\* \* \* \* \*